United States Patent [19]

Hirschbuehler

[11] Patent Number: 4,562,217

[45] Date of Patent: Dec. 31, 1985

[54] CURABLE EPOXY RESIN COMPOSITIONS

[75] Inventor: Kevin Hirschbuehler, Bel Air, Md.

[73] Assignee: American Cyanamid, Stamford, Conn.

[21] Appl. No.: 518,873

[22] Filed: Aug. 1, 1983

[51] Int. Cl.$^4$ ............................ C08K 3/36; C08K 3/04
[52] U.S. Cl. ...................................... 523/466; 523/468
[58] Field of Search ................................ 523/468, 466

[56] References Cited

U.S. PATENT DOCUMENTS 3,932,360 1/1976 Cerankowski et al. .... 260/77.5 AM

FOREIGN PATENT DOCUMENTS

| 52-74655 | 6/1977 | Japan ................................ 523/468 |
| 1017612 | 1/1966 | United Kingdom . |
| 1024288 | 3/1966 | United Kingdom . |
| 1182377 | 2/1970 | United Kingdom . |

OTHER PUBLICATIONS

Gillhan et al., Organic Coatings and Applied Polymer Science Proceedings, vol. 46, pp. 529–598, Mar.-Apr. 1982.
Gillhan et al., Organic Coatings and Applied Polymer Science Proceedings, vol. 48, pp. 566–570, Mar. 1983.
A.C.S. Symposium Series #114, 1979, p. 157.

*Primary Examiner*—Lewis T. Jacobs
*Attorney, Agent, or Firm*—Steven J. Hultquist

[57] ABSTRACT

Curable compositions comprising epoxide prepolymers and polyaminobenzoates, alone, or combined with reinforcements, e.g., graphite fibers, and, optionally modified with second resins. The cured resin fiber matrix compositions exhibit high toughness combined with excellent hot/wet strength.

6 Claims, 3 Drawing Figures

CURABLE EPOXY RESIN COMPOSITIONS

FIELD OF THE INVENTION

This invention relates to improved epoxy resin compositions. In addition, it relates to curable epoxy resin compositions comprising reinforcing filaments and epoxy prepolymers combined with aromatic polyamine curing agents.

CROSS REFERENCE

The following concurrently filed applications are related:

| Serial No. | Applicant(s) |
| --- | --- |
| 518,871 | R. P. Krieger, Jr. |
|  | K. Hirschbuehler |
|  | R. P. Politi |
| 518,872 | D. W. Wang |
|  | J. L. Courter |
|  | D. K. Kohli |
| 518,863 | D. K. Kohli |
| 518,873 | K. Hirschbuehler |
| 518,874 | K. Hirschbuehler |
|  | D. K. Kohli |
| 518,879 | D. R. Draney |
|  | D. K. Kohli |
| 518,856 | D. W. Wang |
|  | D. R. Draney |
| 518,875 | K. Hirschbuehler |

BACKGROUND OF THE INVENTION

Epoxy resin compositions are useful to encapsulate electronic components, and as structural adhesives, and the like. Reinforced epoxy resin composites having high strength to weight ratios have found extensive use in the aircraft and aerospace industries, and in other applications where strength, corrosion resistance and light weight are desirable. For instance, fiber resin matrix materials have replaced aluminum and other metals in primary and secondary structures of modern military and commercial aircraft. Sporting equipment such as tennis rackets and golf clubs have also adopted fiber resin materials successfully.

Epoxy resin compositions and fiber modifications are abundant. Since the advent of fiber resin matrix materials, much effort has been expended in improving their properties and characteristics, including the development of many different curing systems.

Amine and polyamine curing agents have received wide acceptance, but the toxicity, low solubility, high exotherm and variable curing rates seen with the most commonly used amines, such as m-phenylenediamine, 4,4'-diaminodiphenyl methane and 4,4'-diaminodiphenyl sulfone, has made further improvement desirable. In particular, for aircraft structural applications, epoxy resins cured with available curing agents are either too brittle or do not have sufficient strength and stiffness under hot/wet conditions. It is disclosed in U.K. Pat. No. 1,182,377, which is incorporated herein by reference, that certain aromatic polyamines are effective as curing agents for a variety of polyepoxides, and the resulting cured compositions are useful as films, moldings, coatings and glass-reinforced laminates. There is no indication in the properties presented in the U.K. patent that the curing agents exemplified therein will produce the combination of toughness and strength under hot/wet conditions essential for use in the above-mentioned structural applications.

In U.S. Pat. No. 3,932,360, diamine cured polyurethane products are described, in which the diamines are of the formula, e.g.,

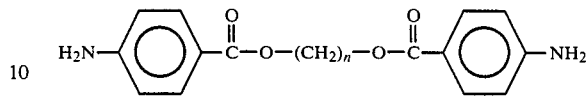

wherein n is an integer from 2 to 12. This U.S. Pat. No. 3,932,360 does not deal with curing compounds having more than one epoxide group per molecule.

In Gillhan et al., Organic Coatings and Applied Polymer Science Proceedings, Vol. 46, p. 592–598, March-April, 1982, polyepoxides cured with diamines of the immediately preceding formula (n is 3), are described.

The present development relates to curable epoxy resin compositions. In one of its aspects, it provides fiber resin matrixes comprising reinforcing filaments in a heat-curable epoxy resin composition comprising an epoxy prepolymer and a novel family of aromatic polyamine curing agents. No member of this novel family of curing agents is specifically exemplified in the U.K. Patent. The invention provides neat resin formulations having, after cure, improved physical properties, e.g., higher elongation and satisfactory hot/wet modulus. The epoxy compositions of the present invention, cured with filaments, exhibit improved interlaminar toughness and residual compression strength after impact, while maintaining compression strength under hot/wet conditions.

SUMMARY OF THE INVENTION

It is an object of the present invention to provide a fiber resin matrix composition that affords satisfactory compression strength over known matrix formulations, especially under hot/wet conditions, and improved compression strength after impact.

These and other objects of the present invention are accomplished herein by a composition comprising:
(a) reinforcing filaments, and
(b) a heat curable epoxy resin composition formed of the following materials:
  (i) N,N,N',N'-tetraglycidyl-4,4'-diaminodiphenyl methane, e.g., 50 to 100, preferably 75 to 85 parts by weight;
  (ii) tetraglycidoxy tetraphenylethane, e.g., 0 to 50, preferably, 15 to 25 parts by weight;
  (iii) trimethylene bis-(p-aminobenzoate), e.g., 28 to 60, preferably 35 to 45 parts by weight;
  (iv) fumed silica, e.g., 0–12, preferably 5 to 7 parts, by weight, and
  (v) the reaction product of toluenediisocyanate and dimethylamine, e.g., 0.1 to 2.5 preferably 0.5 to 1.5 parts by weight.

The fiber resin matrix composition is uniquely suitable for use with an interleaf material to prepare a mechanically superior cured structure.

DESCRIPTION OF THE PREFERRED EMBODIMENTS

Fillers, pigments, dyes, reinforcements, such as glass fibers or woven cloths, plasticizers, and mixtures thereof, may be added to the epoxy resin - polyamine composition before the reaction in order to modify ultimate properties, in known ways. Applications can also be made by trowelling, brush coating, immersion or dip-coating, spraying and other convenient method. Catalysts, such as boron trifluoride - organic amine adducts, and the reaction product of toluene 2,4-diisocyanate and dimethylamine can also be included, in quantities of from e.g., 0.1 to 5% by weight based on the resin - polyamine, to accelerate curing.

The fiber resin matrix compositions according to the present invention can be prepared by embedding filaments, e.g., glass fibers and/or non-siliceous filaments in a curable resin composition to form a fiber resin matrix which can be manipulated and cured to a solid composite. Particular selection of the filament material, with the described epoxy prepolymer(s) and curing agent, as well as including optional ingredients such as fillers, dyes, catalysts, processing aids, etc., can give a range of curable compositions heretofore unknown in the art and exhibiting improved physical properties over known materials.

Glass filaments useful herein are well known. The non-siliceous filament component may be of any non-glass, non-silicon dioxide-containing material which improves the strength or other physical properties of the curable epoxy resin component (described infra.). Such filaments include, but are not limited to, filaments comprised of carbon, graphite, silicon carbide, boron, aramid, polyester, polyamide, rayon, polybenzimidazole, polybenzothiazole, metal-coated such filaments, for example nickel-coated and/or silver-coated graphite fibers and filaments, or combinations of such filaments. Fibers (woven or non-woven), tows or mats of such filaments, or tapes (unwoven, flat bundles of the unidirectional filaments) may be employed as desired. In applications demanding high stiffness to weight ratio or shear strength, carbon fibers, graphite filaments, polyaramid filaments or nickel-plated graphite filaments, as disclosed in assignee's copending application Ser. No. 358,637 are most preferred.

The epoxy resin (b)(i) suitable for the present invention is N,N,N',N'-tetraglycidyl-4,4'-diaminodiphenyl methane.

Preferably, compound (b)(ii) will have the following formula:

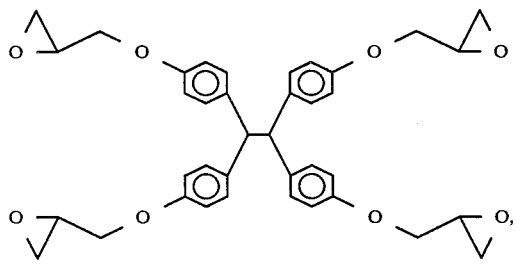

available commercially as EPON ®1031 (Shell).

The primary diamine (b)(iii) will include one or more of a compound of the formula:

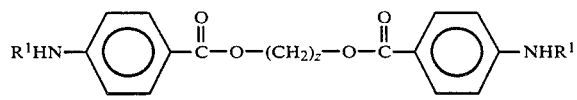

wherein $R^1$ is hydrogen or $C_1$–$C_6$ alkyl, e.g., methyl, and z is an integer of from 2 to 12, preferably 2 to 6, and most preferably 3. Also contemplated are the use of such compounds in combination with other conventional polyamines such as methylene dianiline, phenylene diamine, and the like.

Figure 1:
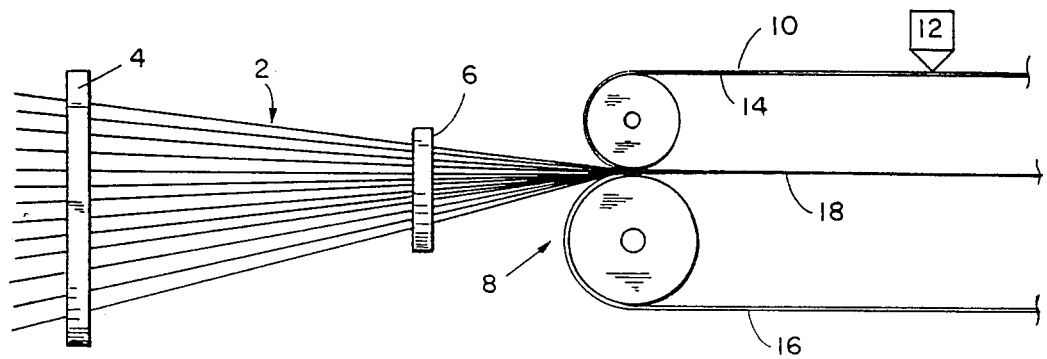
FIG. 1 is a schematic of one method for preparing a fiber resin matrix prepreg tape of the present invention.

One method of forming the fiber matrix composition of the invention is illustrated in the drawings. As seen in FIG. 1, the basic fiber matrix material is produced by delivering fiber 2 through conventional eyeboards 4 and 6 to a pressure roller assembly 8. The resin composition is coated in a layer 10 from a conventional film coating applicator 12 onto a substrate such as release paper 14 and passed through the pressure roller assembly 8. Release paper 16 is also delivered to the pressure roller assembly 8.

The pressure rollers 8 are set at a temperature and pressure for imbedding the fibers 2 in the resin layer 10 to form a fiber matrix composition 18. Practice has taught that a temperature in the range of 190° F. and pressures of one thousand pounds over fifteen inch centers are suitable for producing fiber resin prepreg tape 18.

The fibers 2, the substrate 14 with resin layer 10 and the release paper 16 are delivered to the pressure rollers 8 and passed therethrough at the rate of 5–20 feet/minute.

The feed of fiber 2 and resin layer 10 to the pressure rollers 8 is selected to produce a fiber matrix of about twenty to sixty weight percent resin and about eighty to forty weight percent fiber. For example, one hundred twenty spools of 6K carbon fibers are delivered within a twelve inch width to the pressure rollers 8 with a layer of resin 0.009 to 0.0013 pounds per square foot. The resulting fiber resin matrix 18 results in a generally parallel array of fibers, shown by FIG. 2.

Fillers, pigments, dyes, curing catalysts and other such conventional additives and processing aids may be added to the fiber matrix compositions of the invention before curing to influence the properties of the final resin composite. In addition, polymeric additives such as the butadiene-styrene-acrylonitrile core-shell polymers and the like can be included for their known effects on polymer properties.

The following examples will illustrate the practice of the present invention and are provided by way of demonstration and not by way of limitation.

EXAMPLES 1-3

Three fiber resin matrix formulations were prepared from the following materials:

| | |
|---|---|
| component (a) | CELION ® 6K high strain graphite fiber |
| component (b) (i), (ii) | ARALDITE ® MY720 EPON ® 1031 (see formulae, supra.) |
| (curing agent) (iii) | trimethylene bis-(p-aminobenzoate) |

TABLE 2

| EXAMPLE | CONDITION | 8-PLY UNI | | 16-PLY QUASI | | COMPRESSIVE STRENGTH AFTER IMPACT 36-PLY (KSI) |
| --- | --- | --- | --- | --- | --- | --- |
| | | 23° C. | 93° C. | 23° C. | 93° C. | 1500 in.-lb./in |
| 1 | dry* | 189 | 205 | 84 | 93 | 31.5 |
| | wet* | — | 126 | — | 71 | |
| 2 | dry | 206 | 178 | 87 | 82 | 32.0 |
| | wet | — | 130 | — | 61 | |
| 3 | dry | 205 | 171 | 92 | 74 | 36.0 |
| | wet | — | 12 to 140 (mean, 34)** | — | 45 | |
| Commerical No. 1 | dry | — | — | — | — | 41 |
| Commerical No. 2 | dry | 180 | 175 | 83 | 78 | 28.5 |
| | wet | — | 145 | — | 69 | |
| Commerical No. 3 | dry | — | — | — | — | 20.6 |

*See above.
**For best hot/wet compression strength it would appear that small to moderate excesses of amine are preferred.

| | |
| --- | --- |
| (optional curing agent) | diaminodiphenyl sulfone (DDS) |
| polymer modifier | acrylonitrile-butadiene-styrene, core-shell polymer |
| catalyst | toluene-2,4-diisocyanate reaction product with dimethyl amine |
| filler | fumed colloidal silica (Cab-O-Sil, M-5 Cabot Corp.). |

Figure 2:
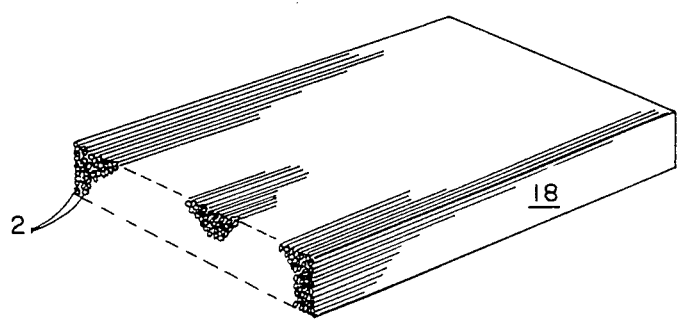
FIG. 2 is an enlarged cross-sectional view of a strip of the fiber resin matrix prepreg tape of the invention.

Using an apparatus shown generally in FIG. 1, prepreg tapes of the structure shown generally in FIG. 2, were prepared:

| | Example | | |
| --- | --- | --- | --- |
| | 1 | 2 | 3 |
| (28%) Resin mixture (parts by weight) | | | |
| N,N,N'N'—tetra(glycidyl-4,4'diaminodiphenyl)methane | 80 | 80 | 80 |
| Tetraglycidoxy tetraphenylethane | 20 | 20 | 20 |
| Trimethylene bis-(para-aminobenzoate) | 44 | 44 | 65 |
| Diaminodiphenyl sulfone | — | — | 20 |
| Polymer modifier* | — | 5 | — |
| Catalyst | 1 | 1 | 1 |
| Fumed silica | 6 | 6 | 6 |
| (72%) Filament (parts by weight) (6K graphite fibers having a strain to failure of about 1.5%) | | | |

*BLENDEX 311, Borg-Warner Co.

These samples were cured and compared against commercial epoxy resin matrixes. The sheets of resin involved were as follows:

| | | |
| --- | --- | --- |
| Uni-Comp: | 8 sheets | [0] |
| Quasi-Comp: | 16 sheets | [(±45/0/90)2]s |
| Comp./Impact: | 36 sheets | [(±45/0/90/0/90)2/±45/0/−90/±45]s |

Figure 3:
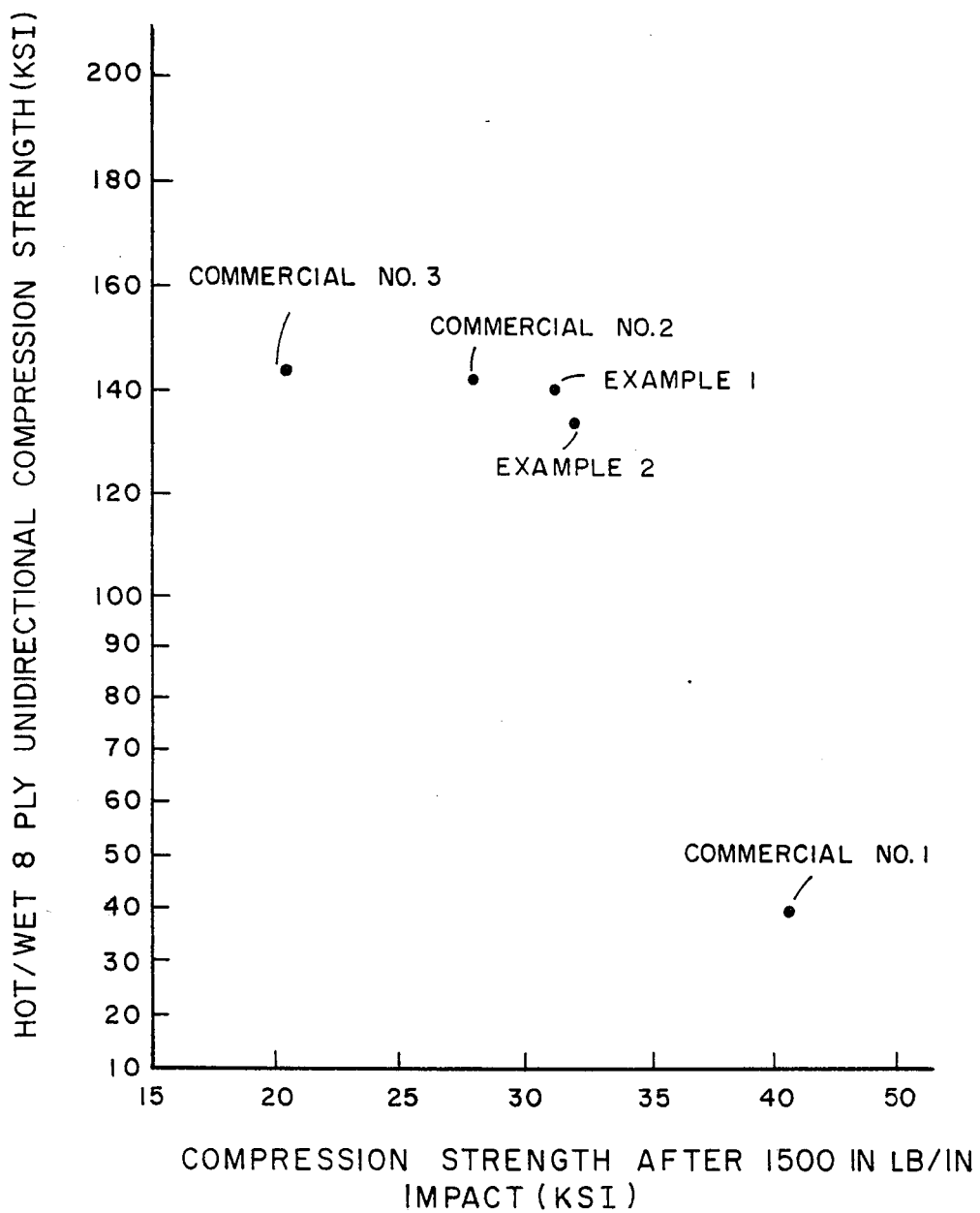
FIG. 3 is a graphical representation comparing hot/wet compressive strength versus dry impact strength for composites according to this invention with state-of-the-art composites.

The compressive strength was measured on a modified ASTM D695 specimen described in D. H. Woolsencraft et al., Composites, Oct., 1981, pages 275–280. Both unidirectional and quasi isotropic laminates were tested by this method. Compressive strength after impact was measured as described in B. A. Byers, NASA Report No. CR 159293, August, 1980. This property is tested by subjecting a cured laminate specimen to 1500 in.-lb. per inch of nominal thickness impact with a 0.62 diameter spherical tip impacter while supported by a rigid base (e.g., 3×5 in. steel cutout). The panel is then tested in compression. The results are set forth in Table 2, as follows:

Some of the foregoing data are represented graphically also in FIG. 3. The data demonstrate that reinforced compositions according to this invention (Examples 1 and 2) have higher compression strength after impact than two of the three commercial compositions, and better hot/wet compression strength than one of them.

The above-mentioned patents, applications and publications are incorporated herein by reference. It is seen that the present invention produces articles of manufacture with beneficial properties, making them useful in a variety of applications. Many variations will suggest themselves to those skilled in this art in light of the foregoing detailed description. All such obvious variations are within the full intended scope of the appended claims.

What is claimed is:

1. A fiber resin matrix composition comprised of:
   (a) reinforcing filaments, and
   (b) a heat-curable epoxy resin composition formed of the following materials:
      (i) N,N,N',N'-tetraglycidyl-4,4'-diaminodiphenyl methane;
      (ii) tetraglycidoxy tetraphenylethane;
      (iii) an effective epoxide curing amount of trimethylene bis-(p-aminobenzoate); and
      (iv) a small, catalytic amount of the reaction product of toluenediisocyanate and dimethylamine.

2. A fiber resin matrix composition comprised of:
   (a) reinforcing filaments, and
   (b) a heat-curable epoxy resin composition formed of the following materials:
      (i) 75–85 parts by weight of N,N,N',N'tetraglycidyl-4,4'-diaminodiphenyl methane;
      (ii) 15–25 parts by weight of tetraglycidoxy tetraphenylethane;
      (iii) 35–45 parts by weight of trimethylene bis-(p-aminobenzoate);
      (iv) 5–7 parts by weight of fumed silica; and
      (v) 0.5–1.5 parts by weight of the reaction product of toluenediisocyanate and dimethylamine.

3. A matrix composition as in claim 1 wherein the resin composition is about 30–40 percent by weight and the filaments are about 70–60 percent by weight.

4. A matrix composition as in claim 1 wherein the filaments comprise carbon or graphite filaments.

5. A matrix composition as in claim 4 wherein the filaments are graphite filaments and they are in generally parallel alignment.

6. A fiber resin matrix composition comprised of:
   (a) reinforcing filaments, and
   (b) a heat-curable epoxy resin composition formed of the following materials:
   (i) 50–100 parts by weight of N,N,N',N'-tetraglycidyl-4,4'-diaminodiphenyl methane;
   (ii) 0–50 parts by weight of tetraglycidoxy tetraphenylethane;
   (iii) 28–60 parts by weight of trimethylene bis-(p-aminobenzoate);
   (iv) 0–12 parts by weight of fumed silica; and
   (v) 0.1–2.5 parts by weight of the reaction product of toluenediisocyanate and dimethylamine.

\* \* \* \* \*